US008409098B2

(12) United States Patent
Olson

(10) Patent No.: US 8,409,098 B2
(45) Date of Patent: Apr. 2, 2013

(54) METHOD AND APPARATUS FOR COLLECTION OF CARDIAC GEOMETRY BASED ON OPTICAL OR MAGNETIC TRACKING

(75) Inventor: Eric S. Olson, Maplewood, MN (US)

(73) Assignee: St. Jude Medical, Atrial Fibrillation Division, Inc., St. Paul, MN (US)

(*) Notice: Subject to any disclaimer, the term of this patent is extended or adjusted under 35 U.S.C. 154(b) by 402 days.

(21) Appl. No.: 12/579,390

(22) Filed: Oct. 14, 2009

(65) Prior Publication Data
US 2011/0087091 A1 Apr. 14, 2011

(51) Int. Cl.
*A61B 8/00* (2006.01)

(52) U.S. Cl. ........ 600/441; 600/407; 600/427; 600/437; 600/447

(58) Field of Classification Search ........... 600/407, 600/427, 437, 441, 447
See application file for complete search history.

(56) References Cited

U.S. PATENT DOCUMENTS

| | | | |
|---|---|---|---|
| 5,379,223 A | 1/1995 | Asplund | |
| 5,592,939 A | 1/1997 | Martinelli | |
| 5,830,210 A | 11/1998 | Rudko et al. | |
| 6,019,725 A | 2/2000 | Vesely et al. | |
| 6,104,944 A | 8/2000 | Martinelli | |
| 6,216,026 B1 | 4/2001 | Kuhn et al. | |
| 6,233,476 B1 | 5/2001 | Strommer et al. | |
| 6,236,875 B1 | 5/2001 | Bucholz et al. | |
| 6,246,898 B1 | 6/2001 | Vesely et al. | |
| 6,317,621 B1 | 11/2001 | Graumann et al. | |
| 6,368,285 B1 | 4/2002 | Osadchy et al. | |
| 6,490,467 B1 | 12/2002 | Bucholz et al. | |
| 6,493,573 B1 | 12/2002 | Martinelli et al. | |
| 6,556,695 B1 | 4/2003 | Packer et al. | |
| 6,623,431 B1 | 9/2003 | Sakuma et al. | |
| 6,663,625 B1 | 12/2003 | Ormsby et al. | |
| 6,774,624 B2 | 8/2004 | Anderson et al. | |
| 6,783,536 B2 | 8/2004 | Vilsmeier et al. | |
| 6,892,090 B2 | 5/2005 | Verard et al. | |
| 6,895,267 B2 | 5/2005 | Panescu et al. | |
| 6,920,347 B2 | 7/2005 | Simon et al. | |

(Continued)

FOREIGN PATENT DOCUMENTS

| | | |
|---|---|---|
| AU | 2008100107 | 3/2008 |
| WO | WO 03/107275 | 12/2003 |

(Continued)

*Primary Examiner* — Unsu Jung
*Assistant Examiner* — Joel Lamprecht
(74) *Attorney, Agent, or Firm* — Dykema Gossett PLLC

(57) ABSTRACT

A cardiac imaging system including an imaging module including an ultrasound emitter and one or more position markers. A tracking and control system may include a position sensing system for sensing a location and orientation of the position marker relative to a predetermined reference. The tracking and control system may be operable with the imaging module to produce at least a three dimensional image of a patient's anatomy. A method of cardiac imaging may include operatively attaching one or more position markers to an imaging module including an ultrasound emitter. The method may further include sensing a location and orientation of the position marker relative to a predetermined reference, and producing at least a three dimensional image of a patient's anatomy by evaluating one or more images obtained by the imaging module and aligning the image(s) obtained by the imaging module relative to the location and orientation of the position marker.

20 Claims, 8 Drawing Sheets

U.S. PATENT DOCUMENTS

| | | |
|---|---|---|
| 6,947,786 B2 | 9/2005 | Simon et al. |
| 6,968,224 B2 | 11/2005 | Kessman et al. |
| 6,990,368 B2 | 1/2006 | Simon et al. |
| 7,007,699 B2 | 3/2006 | Martinelli et al. |
| 7,015,859 B2 | 3/2006 | Anderson |
| 7,089,063 B2 | 8/2006 | Lesh et al. |
| 7,103,399 B2 | 9/2006 | Miga et al. |
| 7,139,601 B2 | 11/2006 | Bucholz et al. |
| 7,211,082 B2 | 5/2007 | Hall et al |
| 7,263,397 B2 | 8/2007 | Hauck et al. |
| 7,343,195 B2 | 3/2008 | Strommer et al. |
| 7,604,601 B2 | 10/2009 | Altmann et al. |
| 7,981,038 B2 | 7/2011 | Kanade et al. |
| 2001/0031919 A1 | 10/2001 | Strommer et al. |
| 2001/0047133 A1 | 11/2001 | Gilboa et al. |
| 2002/0042571 A1 | 4/2002 | Gilboa et al. |
| 2002/0049375 A1 | 4/2002 | Strommer et al. |
| 2002/0193686 A1 | 12/2002 | Gilboa |
| 2003/0114778 A1 | 6/2003 | Vilsmeier et al. |
| 2003/0160721 A1 | 8/2003 | Gilboa et al. |
| 2003/0216639 A1 | 11/2003 | Gilboa et al. |
| 2004/0015079 A1* | 1/2004 | Berger et al. ................ 600/437 |
| 2004/0030244 A1 | 2/2004 | Garibaldi et al. |
| 2004/0054248 A1* | 3/2004 | Kimchy et al. ................ 600/3 |
| 2004/0087996 A1 | 5/2004 | Gambale et al. |
| 2004/0097805 A1 | 5/2004 | Verard et al. |
| 2004/0097806 A1 | 5/2004 | Hunter et al. |
| 2004/0147837 A1 | 7/2004 | Macaulay et al. |
| 2004/0242995 A1 | 12/2004 | Maschke |
| 2004/0249267 A1 | 12/2004 | Gilboa |
| 2005/0049510 A1 | 3/2005 | Haldeman et al. |
| 2005/0054910 A1* | 3/2005 | Tremblay et al. ............ 600/411 |
| 2005/0137661 A1 | 6/2005 | Sra |
| 2005/0148853 A1 | 7/2005 | Redel |
| 2005/0148859 A1 | 7/2005 | Miga et al. |
| 2005/0182319 A1 | 8/2005 | Glossop |
| 2005/0203394 A1 | 9/2005 | Hauck et al. |
| 2005/0288577 A1 | 12/2005 | Weese |
| 2006/0009755 A1 | 1/2006 | Sra |
| 2006/0084867 A1* | 4/2006 | Tremblay et al. ............ 600/434 |
| 2006/0116575 A1 | 6/2006 | Willis |
| 2006/0116576 A1 | 6/2006 | McGee et al. |
| 2006/0122514 A1 | 6/2006 | Byrd et al. |
| 2006/0144407 A1 | 7/2006 | Aliberto et al. |
| 2006/0173287 A1 | 8/2006 | Sabczynski et al. |
| 2006/0184016 A1 | 8/2006 | Glossop |
| 2006/0247522 A1 | 11/2006 | McGee |
| 2007/0016005 A1 | 1/2007 | Timinger et al. |
| 2007/0021744 A1 | 1/2007 | Creighton |
| 2007/0055141 A1 | 3/2007 | Kruger et al. |
| 2007/0073288 A1 | 3/2007 | Hall et al. |
| 2007/0135713 A1 | 6/2007 | Borgert et al. |
| 2007/0167738 A1 | 7/2007 | Timinger et al. |
| 2007/0179496 A1 | 8/2007 | Swoyer et al. |
| 2007/0197905 A1 | 8/2007 | Timinger et al. |
| 2007/0232898 A1 | 10/2007 | Huynh et al. |
| 2007/0276216 A1 | 11/2007 | Beyar et al. |
| 2007/0287909 A1 | 12/2007 | Garibaldi et al. |
| 2007/0293721 A1 | 12/2007 | Gilboa |
| 2008/0006280 A1 | 1/2008 | Aliberto et al. |
| 2008/0015670 A1 | 1/2008 | Pappone |
| 2008/0021297 A1 | 1/2008 | Boosten |
| 2008/0051721 A1 | 2/2008 | Carter et al. |
| 2008/0119785 A1 | 5/2008 | Ramsey et al. |
| 2009/0163810 A1 | 6/2009 | Kanade et al. |
| 2009/0171196 A1 | 7/2009 | Olson et al. |
| 2009/0171201 A1 | 7/2009 | Olson |

FOREIGN PATENT DOCUMENTS

| | | |
|---|---|---|
| WO | WO 2007/044792 | 4/2007 |

\* cited by examiner

METHOD AND APPARATUS FOR COLLECTION OF CARDIAC GEOMETRY BASED ON OPTICAL OR MAGNETIC TRACKING

BACKGROUND OF THE INVENTION a. Field of the Invention

The invention relates to imaging systems for use in the performance of medical diagnostic, therapeutic, mapping and ablative procedures. More particularly, the invention relates to an imaging system including optical or magnetic tracking for generating accurate 2D or 3D time varying images.

b. Background Art

A variety of imaging systems can be used to assist a clinician or physician in the performance of various medical diagnostic and therapeutic procedures related to different parts of the human anatomy, such as, the heart. Such imaging systems include, for example, those based on a variety of technologies, such as, wands (e.g. ultrasound), (fluoroscopy (e.g., x-rays), computed tomography (CT), magnetic resonance (MR), and intracardiac echocardiography (ICE). For ultrasound wands, an ultrasound emitter may be disposed in the wand, or in the case of catheters (e.g. ICE (intra-cardiac echo) or TEE (transesophageal echo)), the ultrasound emitter may be disposed in the catheter.

In the case of a wand, the wand may be placed on the skin of a patient and typically, 2D image slices may be collected. Alternatively, the wand may also contain a rotating sensor, or the wand itself may be rotated on a mechanical rotation device for collecting 3D images. In both cases, images are continuously collected so that CINE (e.g. real-time animated views) images are possible, thus making the 2D and 3D images, 3D and 4D respectively, with the additional dimension being time.

Based on the data collected by the wand, it is also possible to automatically extract the shape of an internal body structure using automatic segmentation algorithms. By evolving the segmented static models over time, time varying surface models can also be generated.

A drawback of these methods is that the various images collected by the wand are not registered together. In other words, since the ultrasound wand may be moved or tilted, the images from different points of time are not aligned with each other. For example, if parallel images are desired and the ultrasound wand is tilted as images are being taken, the images essentially will not be parallel. Moreover, since the wand can be manually or even mechanically rotated, there can be various gaps in the disparate images.

The inventors herein have thus recognized a need for a system and method for precise and automatic correlation of such images, regardless of whether a wand is manually or mechanically rotated or tilted, thus freeing an operator to move a wand with limited constraints. The inventors herein have also recognized a need for a system and method for providing guidance for such imaging, and a system that is capable of extrapolating omitted image data.

BRIEF SUMMARY OF THE INVENTION

A cardiac imaging system may include an imaging module including an ultrasound emitter and one or more position markers. A tracking and control system may include a position sensing system for sensing a location and orientation of the position marker relative to a predetermined reference. The tracking and control system may be operable with the imaging module to produce at least a three dimensional image of a patient's anatomy.

For the cardiac imaging system described above, in an embodiment, the imaging module may be a hand-held module disposable against the patient's skin. Alternatively, in an embodiment, the imaging module may be operatively connected to a catheter. In an embodiment, the imaging module may be a two dimensional imaging module, with the third dimension of the three dimensional image produced by the tracking and control system being time. The imaging module, in an embodiment, may be a three dimensional imaging module, with the tracking and control system producing a four dimensional image, and the fourth dimension being time. In an embodiment, the three dimensional image may be a CINE image. The position marker, in an embodiment, may emit an infrared signal sensed by the position sensing system.

For the cardiac imaging system described above, in an embodiment, the position marker may include one or more optical fiducial markers. In an embodiment, the optical fiducial marker(s) may be a spherical marker that reflects infrared light emitted by illuminators on the position sensing system. In an embodiment, the cardiac imaging system may include a plurality of the optical fiducial markers disposed in a predetermined arrangement. The predetermined arrangement, in an embodiment, may be a generally triangular pyramid-shaped arrangement. The predetermined arrangement, in an embodiment, may be a generally symmetrical arrangement. In an embodiment, the cardiac imaging system may include one or more further optical fiducial markers disposed against a moving part of the patient's anatomy being imaged, with the further optical fiducial marker(s) serving as a moving reference for the position sensing system.

For the cardiac imaging system described above, in an embodiment, the position marker may include one or more magnetic markers. In an embodiment, the magnetic marker(s) may be operably connected to or disposed inside the imaging module. In an embodiment, the cardiac imaging system may further include a magnetic emitter operably connected to the position sensing system, with the magnetic emitter emitting a magnetic field for sensing a location and orientation of the magnetic marker.

For the cardiac imaging system described above, in an embodiment, the imaging system may be operably connected to a robotic catheter system for automatic cardiac imaging. In an embodiment, the imaging system may include a visualization sub-system for displaying the image of the patient's anatomy. The imaging system, in an embodiment, may be operably connected to a navigation and mapping sub-system. In an embodiment, the imaging system may be used to track and/or navigate an interventional device. In an embodiment, the interventional device may be a catheter.

For the cardiac imaging system described above, in an embodiment, the tracking and control system may produce the three dimensional image by processing a plurality of images obtained by the imaging module using automatic segmentation algorithms. In an embodiment, the tracking and control system may automatically align an image obtained by the imaging module relative to the predetermined reference. The tracking and control system, in an embodiment, may automatically align a plurality of images obtained by the imaging module relative to the predetermined reference to generate the three dimensional image. In an embodiment, the tracking and control system may automatically align a plurality of images obtained by the imaging module relative to the predetermined reference to generate a three dimensional time-varying image, with the tracking and control system further ascertaining gaps in the three dimensional time-varying image. In an embodiment, the tracking and control system may automatically complete any ascertained gaps. The tracking and control system, in an embodiment, may prompt a user to obtain further images for completing any ascertained gaps, for example, when aggregating a plurality of 2D images into a 3D image.

In an embodiment, a method of cardiac imaging may include operatively attaching one or more position markers to an imaging module including an ultrasound emitter, and sensing a location and orientation of the position marker(s) relative to a predetermined reference. The method may further include producing at least a three dimensional image of a patient's anatomy by evaluating one or more image(s) obtained by the imaging module and aligning the image(s) obtained by the imaging module relative to the location and orientation of the position marker.

For the method described above, the method may further include disposing the imaging module against the patient's skin to produce the image obtained by the imaging module. In an embodiment, the method may further include operatively connecting the imaging module to a catheter. The imaging module, in an embodiment, may be a two dimensional imaging module, with the third dimension of the three dimensional image being time. In an embodiment, the imaging module may be a three dimensional imaging module, with the method further including producing a four dimensional image, and the fourth dimension being time. In an embodiment, the three dimensional image may be a CINE image. The position marker, in an embodiment, may emit an infrared signal.

In an embodiment, the position marker may include one or more optical fiducial markers. The optical fiducial marker(s), in an embodiment, may be a spherical marker that reflects infrared light emitted by illuminators on a position sensing system. In an embodiment, the method may further include providing a plurality of the optical fiducial markers in a predetermined arrangement. The predetermined arrangement, in an embodiment, may be a generally triangular pyramid-shaped arrangement. In an embodiment, the predetermined arrangement may be a generally symmetrical arrangement. The method, in an embodiment, may further include disposing one or more further optical fiducial markers against a moving part of the patient's anatomy being imaged, with the further optical fiducial marker(s) serving as a moving reference.

In an embodiment, the method may further include providing a position marker including one or more magnetic markers. The magnetic marker(s) may be operably connected to or disposed inside the imaging module. In an embodiment, the method may further include providing a magnetic emitter for emitting a magnetic field for sensing the location and orientation of the magnetic marker. The method may, in an embodiment, further include using the three dimensional image with a robotic catheter system. In an embodiment, the method may include displaying the image of the patient's anatomy. The method, in an embodiment, may include navigation and mapping.

In an embodiment, the method may further include tracking and navigating an interventional device. In an embodiment, the interventional device may be a catheter. In an embodiment, the method may further include producing the three dimensional image by processing a plurality of images obtained by the imaging module using automatic segmentation algorithms. The method, in an embodiment, may further include automatically aligning the image obtained by the imaging module relative to the predetermined reference. In an embodiment, the method may include automatically aligning a plurality of images obtained by the imaging module relative to the predetermined reference to generate the three dimensional image. In an embodiment, the method may include automatically aligning a plurality of images obtained by the imaging module relative to the predetermined reference to generate a three dimensional time-varying image, and further ascertaining gaps in the three dimensional time-varying image. The method, in an embodiment, may further include automatically completing any ascertained gaps. In an embodiment, the method may further include automatically prompting a user to obtain further images for completing any ascertained gaps.

The foregoing and other aspects, features, details, utilities, and advantages of the invention will be apparent from reading the following description and claims, and from reviewing the accompanying drawings.

DETAILED DESCRIPTION OF THE INVENTION

Figure 1:
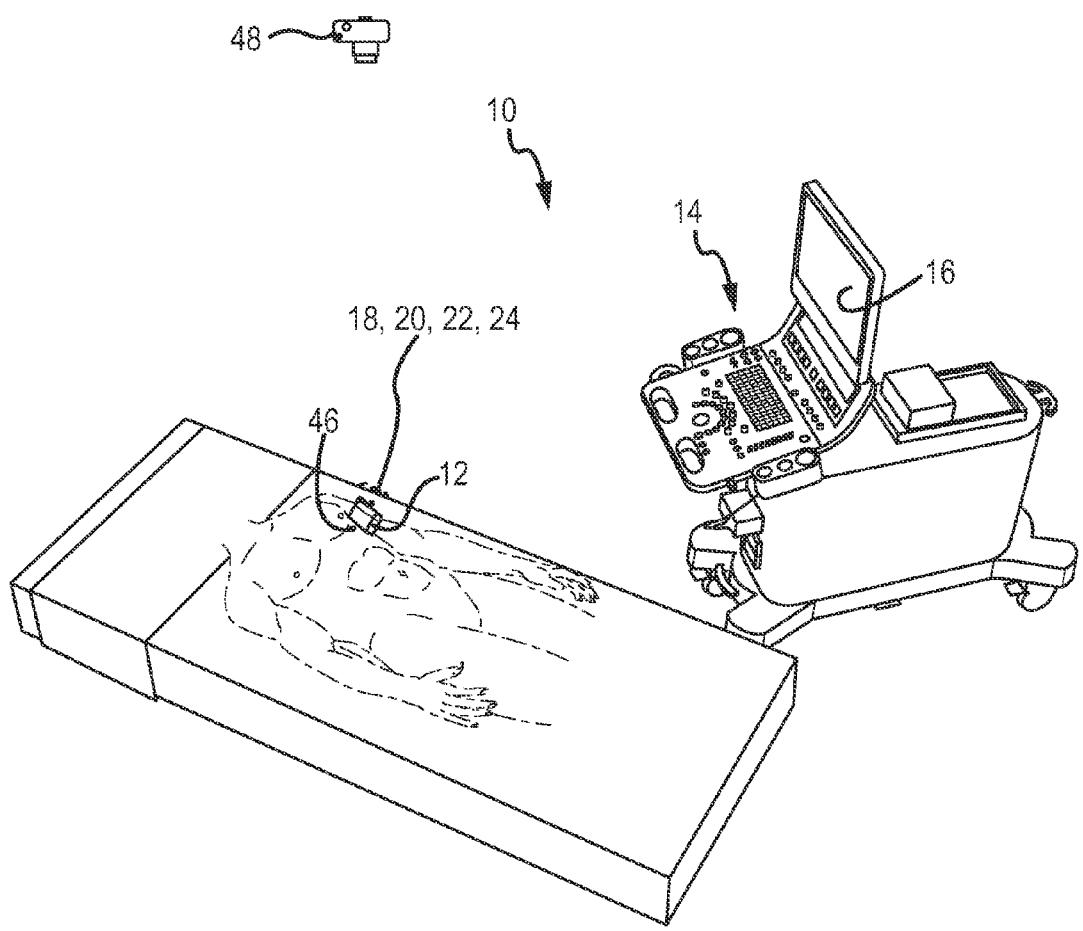
FIG. 1 is a diagrammatic view of an exemplary embodiment of an optical-based imaging system in accordance with the invention, illustrating an enlarged view of a portion of a patient's body with an optical-based imaging module being used adjacent a patient's heart area.
Figure 1:
Figure 1:

Referring now to the drawings wherein like reference numerals are used to identify identical components in the various views, FIG. 1 illustrates an optical-based imaging system 10 in accordance with the invention. Imaging system 10 may be configured to image desired internal anatomic structures of a patient, may be used to track and/or navigate interventional devices, and may be usable in combination with a robotic catheter system (e.g. disclosed in commonly owned and copending applications titled "Robotic Catheter System," "Robotic Catheter Manipulator Assembly," "Robotic Catheter Device Cartridge," "Robotic Catheter Rotatable Device Cartridge," "Robotic Catheter Input Device," "Robotic Catheter System Including Haptic Feedback," and "Robotic Catheter System with Dynamic Response," the respective disclosures of which are incorporated herein by reference in their entirety). Accordingly, imaging system 10 may also be considered an "imaging and navigation" system rather than simply an "imaging" system.

As shown in FIG. 1 and described in detail below, optical-based imaging system 10 may generally incorporate an optical-based imaging module 12 (including an ultrasound emitter (not shown)), a tracking and control system 14, and a visualization system 16 that provides a user with real-time or near-real-time positioning information, partial or complete images generated by system 10, and guidance for imaging module 12. Other systems, such as an EnSite® NavX system (not shown) may be incorporated with imaging system 10 for providing closed-loop feedback and further visualization, navigation, and mapping. Control system 14 incorporates ultrasound imaging and optical based tracking.

Figure 2:
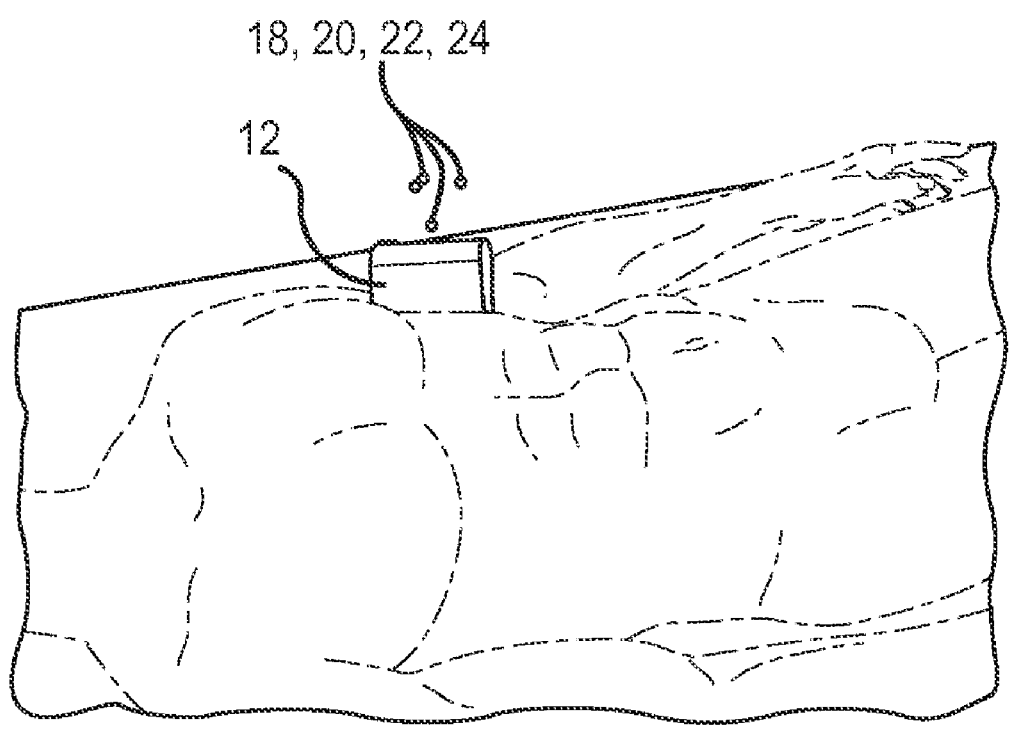
FIG. 2 is an enlarged diagrammatic view of the portion of the patient's body and the optical-based imaging module of FIG. 1.

As discussed herein, the ultrasound emitter may alternatively be disposed in a catheter (e.g. ICE (intra-cardiac echo) or TEE (transesophageal echo)), with both embodiments using the imaging module and catheter usable with the aforementioned robotic catheter system. A plurality of strategically disposed optical fiducial markers (e.g. spherical, retro-reflective markers that reflect infrared light emitted by illuminators on a position sensing system (not shown)) 18, 20, 22 and 24 may be symmetrically placed on imaging module 12 for allowing the position and orientation of module 12 to be determined in 6D (e.g. x, y, z and rotational along each axis) by tracking and control system 14. In an exemplary embodiment, tracking and control system 14 may employ an optical tracking sub-system such as the Polaris Spectra and Polaris Vicra optical tracking systems available from Northern Digital, or another triangulation based optical tracking sub-system. In the embodiment illustrated, optical fiducial markers 18, 20, 22 and 24 may be disposed in a three-dimensional pyramid shape with equal triangles as shown in FIG. 2, and attached to a framed or another structure (not shown) to imaging module 12. A series of three or more cameras 48 may be generally positioned as shown for tracking the movement (e.g. position and orientation) of markers 18, 20, 22 and 24, which are disposed, for example, 10 cm apart.

Generally, the optical tracking sub-system of tracking and control system 14 may provide for location and orientation measurement of imaging module 12 by means of a position sensing system operatively provided with cameras 48 and incorporated with tracking and control system 14. The position sensing system may detect the position and orientation of optical fiducial markers 18, 20, 22 and 24 within a defined coordinate system in the vicinity of imaging system 10, and calculate the position and orientation of imaging module 12 based on the information received from the markers. In an embodiment, instead of optical fiducial markers 18, 20, 22 and 24, alternatively, infrared-emitting markers may also be used.

Figure 3:
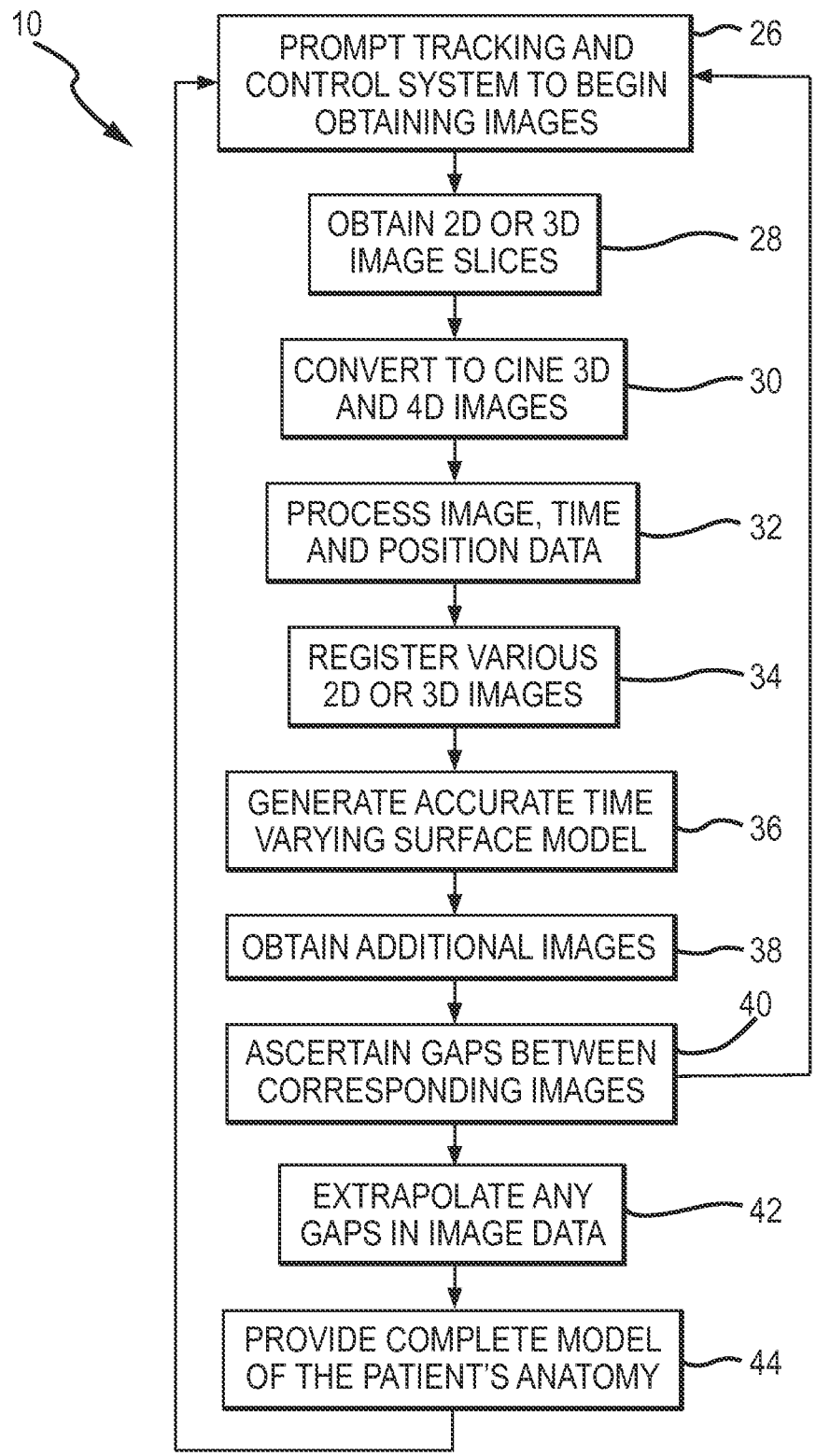
FIG. 3 is an exemplary flowchart of the operation of the optical-based imaging system of FIG. 1.

Referring to FIGS. 1-3, with the position and orientation of imaging module 12 determinable, a user (such as an EP) may place imaging module 12 against the skin of a patient as shown in FIGS. 1 and 2, and then prompt tracking and control system 14 to begin obtaining images at location 26 (see flowchart of FIG. 3) of the patient's anatomy while tracking movement of module 12. Imaging module 12 may then obtain 2D or 3D image slices at location 28, which may be converted to CINE 3D and 4D images at location 30. The image, time and position (e.g. position and orientation) data may then be processed at location 32 by tracking and control system 14 to automatically extract the shape of the patient's anatomy using, for example, automatic segmentation algorithms, such as, active template/shape models, snakes, level sets and fast marching methods. Exemplary applications of such techniques are disclosed in commonly owned and copending U.S. application Ser. No. 11/967,412 titled "Method and Apparatus for Encoding Interventional Devices," and U.S. application Ser. No. 11/967,788, titled "Method and Apparatus for Real-Time Hemodynamic Monitoring," the respective disclosures of which are incorporated herein by reference. Based on the predefined coordinate system set as a reference for tracking and control system 14, system 14 may register (e.g. align) the various 2D or 3D images at location 34 obtained by imaging module 14 relative to the coordinate system. Tracking and control system 14 may also process the data to evolve the segmented static models over time, to thus generate accurate, for example, 1 mm or less location accuracy, time varying surface models at location 36.

Still referring to FIGS. 1-3, with the images generated by imaging module 12 registered as discussed above, tracking and control system 14 may then prompt the user at location 38 to obtain additional images on any omitted areas to thus generate a complete model of the patient's anatomy. Further, tracking and control system 14 may ascertain at location 40, based on predetermined parameters, any gaps between corresponding images to determine whether additional images are needed or if the gaps may be completed by extrapolation. If no gaps are present, at locations 26 and 40, the user may then re-prompt tracking and control system 14 to obtain other images on the same or a different patient. In the latter case if gaps are present, tracking and control system 14 may extrapolate at location 42 any gaps in the image data to provide at location 44 a complete model of the patient's anatomy. At locations 26 and 44, the user may then re-prompt tracking and control system 14 to obtain other images on the same or a different patient. Tracking and control system 14 may also guide the user by suggesting increased or decreased tilting of imaging module 12 in order to obtain any missing data, and further alert the user when the data has been successfully captured. Thus by ascertaining the 6D position of imaging module 12, the position of the collected image in Cartesian coordinates may be determined through the assumption that the image is rigidly related to module 12.

Figure 4:
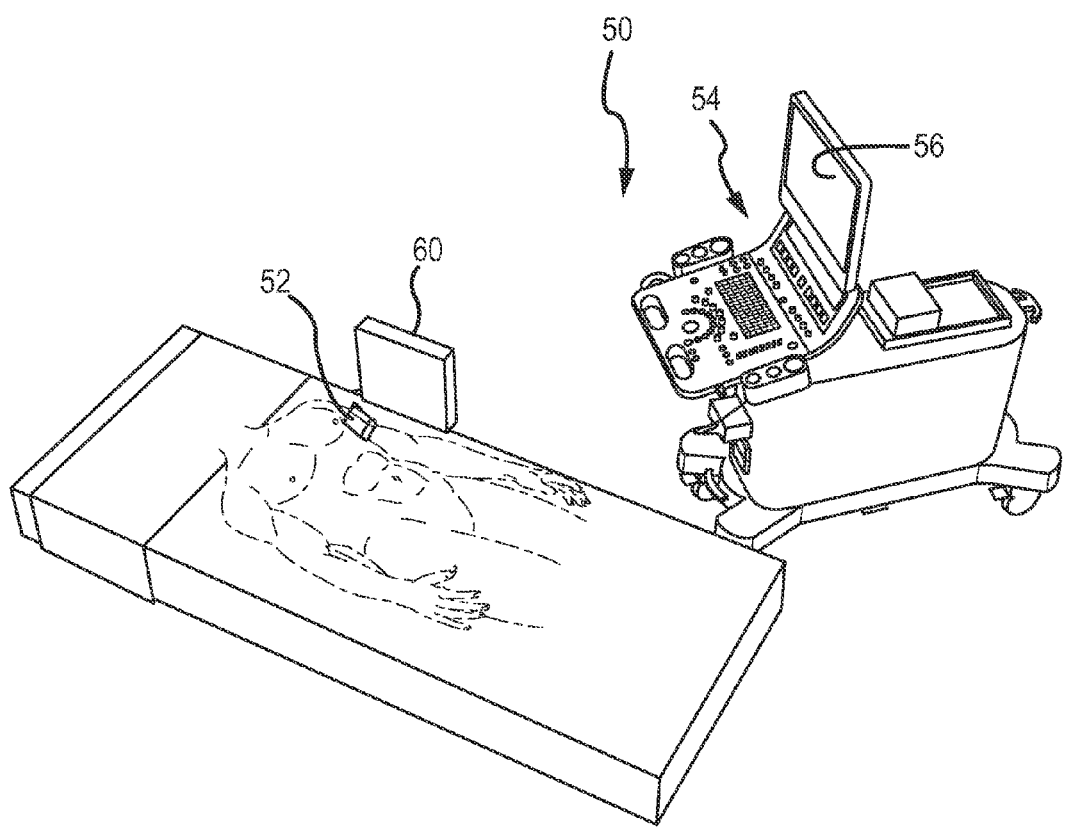
FIG. 4 is a diagrammatic view of an exemplary embodiment of a magnetic-based imaging system in accordance with the invention, illustrating an enlarged view of a portion of a patient's body with a magnetic-based imaging module being used adjacent a patient's heart area.
Figure 5:
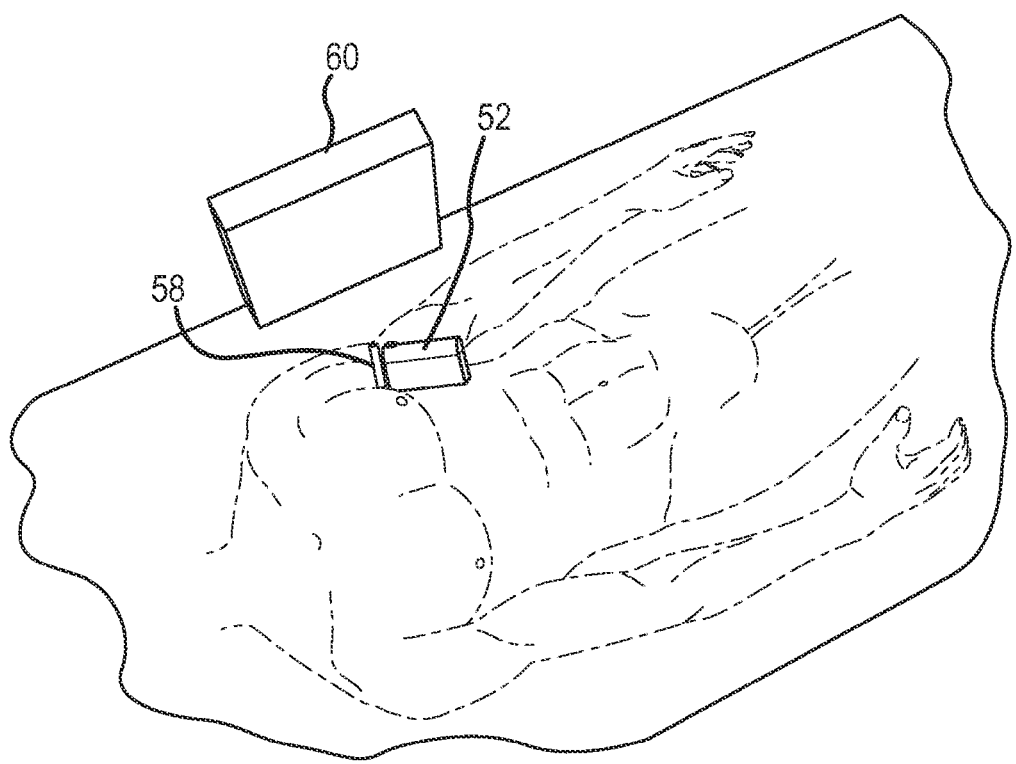
FIG. 5 is an enlarged diagrammatic view of the portion of the patient's body and the magnetic-based imaging module of FIG. 4.
Figure 6:
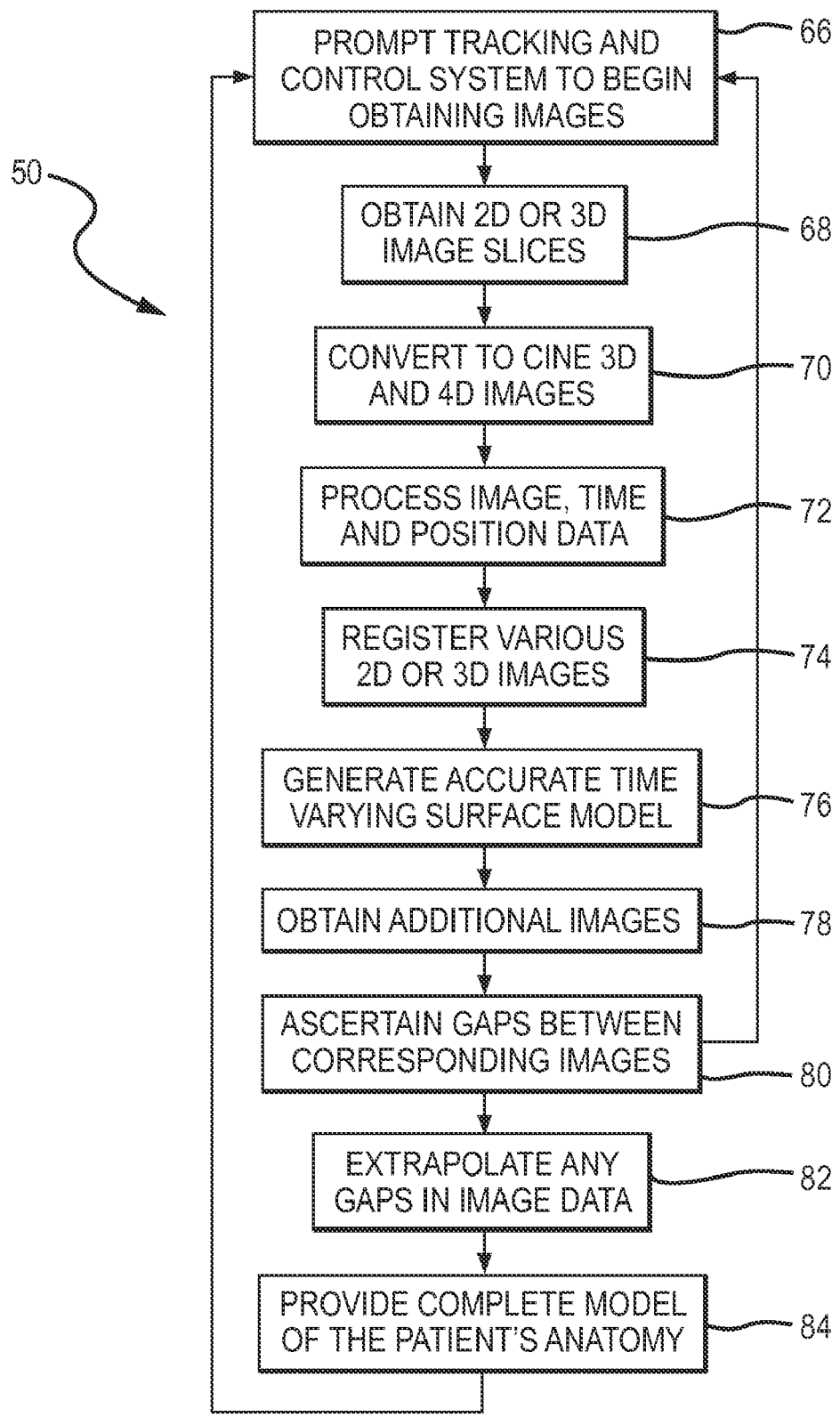
FIG. 6 is an exemplary flowchart of the operation of the magnetic-based imaging system of FIG. 4.

Referring to FIGS. 4-6, an embodiment of a magnetic-based imaging system 50 incorporating a magnetic-based imaging module 52 will be described in detail.

Referring to FIGS. 4 and 5, imaging module 52, similar to imaging module 12, may generally include an ultrasound emitter (not shown). As discussed above, similar to imaging module 12, the ultrasound emitter may alternatively be disposed in a catheter (e.g. ICE (intra-cardiac echo) or TEE (transesophageal echo)), with both embodiments using the imaging module and catheter usable with the aforementioned robotic catheter system. A 6D (e.g. x, y, z and rotational along each axis) magnetic sensor 58 (see FIG. 5) may be attached to or disposed inside the frame of imaging module 52 for allowing the position and orientation of module 52 to be determined by tracking and control system 54, with the subsequently generated images being displayed on visualization system 56. Magnetic sensor 58 may generally include at least two magnetic coils that are disposed transverse to each other. An emitter 60 may be disposed adjacent magnetic sensor 58 as shown in FIG. 5 for emitting magnetic fields and thereby sensing the position and orientation of imaging module 52. In a particular embodiment, tracking and control system 54 may employ a magnetic tracking sub-system such as the Aurora magnetic tracking system available from Northern Digital, or other similar devices available from Ascension Technology Corporation.

Generally, the magnetic tracking sub-system of tracking and control system 54 may provide for location and orientation measurement of imaging module 52 by means of magnetic sensor 58 and a position sensing system (not shown) incorporated with emitter 60 of tracking and control system 54. The position sensing system may detect the position and orientation of magnetic sensor 58 within a defined coordinate system in the vicinity of imaging system 50, and calculate the position and orientation of imaging module 52 based on the information received from the sensor.

Referring to FIGS. 4-6, with the position and orientation of imaging module 52 determinable, a user (such as an EP) may place imaging module 52 against the skin of a patient as shown in FIGS. 4 and 5, and then prompt tracking and control system 54 to begin obtaining images at location 66 (see flow-chart of FIG. 6) of the patient's anatomy while tracking movement of module 52. Imaging module 52 may then obtain 2D or 3D image slices at location 68, which may be converted to CINE 3D and 4D images at location 70. The image, time and position (e.g. position and orientation) data may then be processed at location 72 by tracking and control system 54 to automatically extract the shape of the patient's anatomy using, for example, automatic segmentation algorithms, in a similar manner as that for imaging system 10. Based on the predefined coordinate system set as a reference for tracking and control system 54, system 54 may register (e.g. align) the various 2D or 3D images at location 74 obtained by imaging module 52 relative to the coordinate system. Tracking and control system 54 may also process the data to evolve the segmented static models over time, to thus generate an accurate, for example, 1 mm or less location accuracy, time varying surface model at location 76.

Still referring to FIGS. 4-6, with the images generated by imaging module 52 registered as discussed above, tracking and control system 54 may then prompt the user at location 78 to obtain additional images on any omitted areas to thus generate a complete model of the patient's anatomy. Further, tracking and control system 54 may ascertain at location 80, based on predetermined parameters, any gaps between corresponding images to determine whether additional images are needed or if the gaps may be completed by extrapolation. If no gaps are present, at locations 66 and 80, the user may then re-prompt tracking and control system 54 to obtain other images on the same or a different patient. In the latter case if gaps are present, tracking and control system 54 may extrapolate at location 82 any gaps in the image data to provide at location 84 a complete model of the patient's anatomy. At locations 66 and 84, the user may then re-prompt tracking and control system 54 to obtain other images on the same or a different patient. Thus by knowing the 6D position of imaging module 52, the position of the collected image in Cartesian coordinates may be determined through the assumption that the image is rigidly related to module 52.

In another embodiment, whereas for the embodiments of FIGS. 1-6 may utilize a distant reference point (e.g. adjacent a patient's bed) for generating the 3D or 4D images, in the case of a beating heart for example, a patient's anatomy may constantly change relative to time. Referring to FIG. 1, a secondary reference sensor 46 may be placed, for example, adjacent a patient's heart area or internally (likewise for FIG. 4). By using this secondary reference sensor, any generated images may be aligned relative to each other and relative to moving sensor 46. This would allow the origin of the reference point to be constantly updated to ensure accurate imaging.

Imaging systems 10, 50 are beneficial in that based on the tracking by respective tracking and control systems 14, 54, 2D imaging modules 12, 52 (instead of optional 3D imaging modules) may be used to collect 3D data by manual rotation of the modules about an axis normal to the patient. Because of the tracking provided by systems 14, 54, imaging modules 12, 52 may be maneuvered (rotated or translated) in a predetermined pattern, without specific focus on the positional/orientation control of the modules, thus potentially negating the need for a precision mechanical rotation/movement device. For example, imaging modules 12, 52 may be positioned adjacent a patient's heart or other anatomy and moved virtually randomly in that area to obtain a series of images by tracking and control systems 14, 54 to generate a 3D volumetric image of the patient's anatomy. However if a predetermined area of a patient's anatomy is of importance, imaging modules 12, 52 may be moved in a predetermined pattern in those areas to generate a 3D volumetric image without unnecessary computations due to random movement of the modules.

With regard to 4D volumetric images, instead of a 3D volume, tracking and control systems 14, 54 may capture a plurality of images with respect to time and in the case of a heart for example, systems 14, 54 may place the images in the correct phase to create separate 4D volumetric images.

Figure 7:
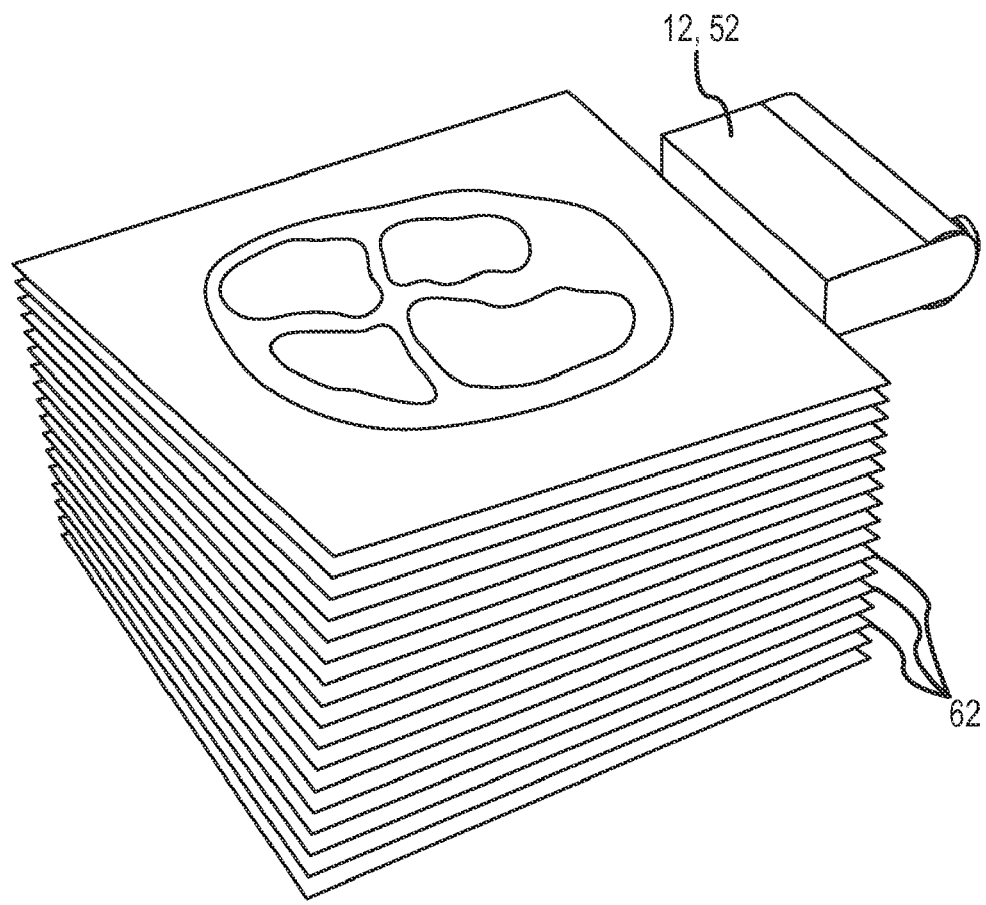
FIG. 7 shows exemplary image slices obtained by the imaging modules of FIGS. 1 and 4, and displayed on a visualization system.
Figure 8:
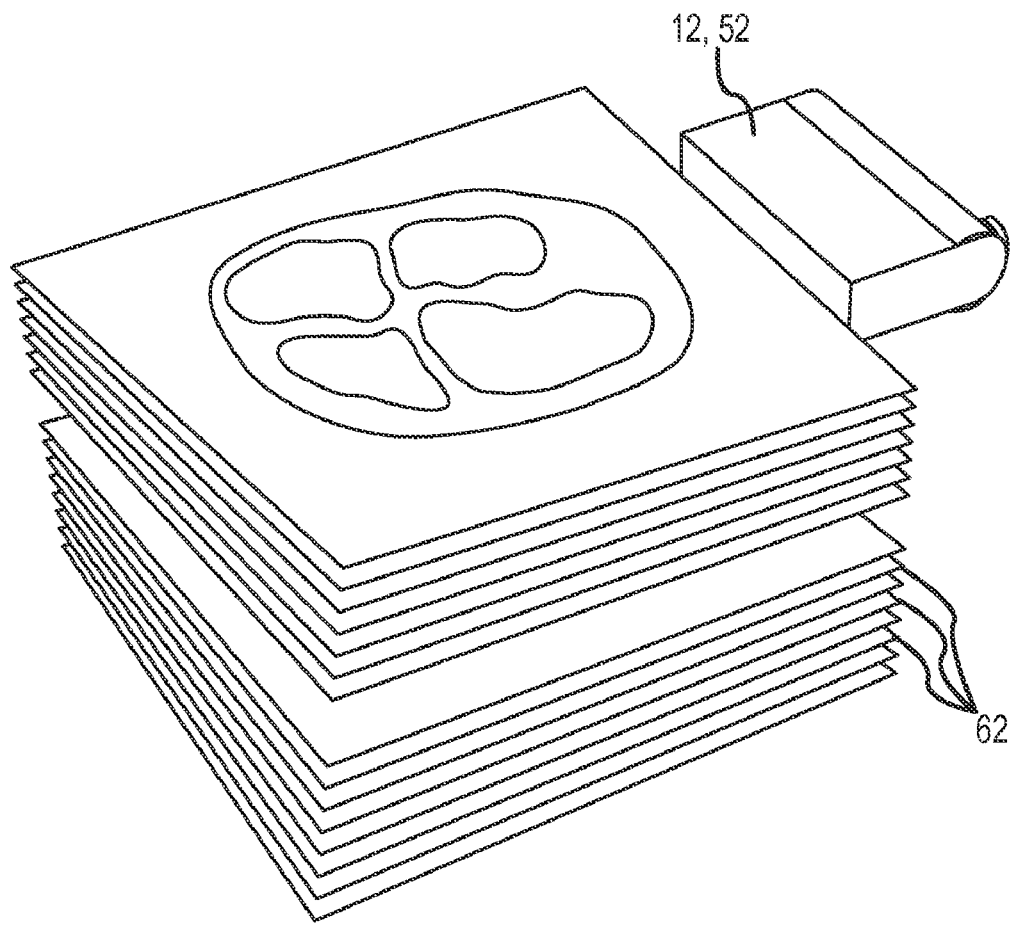
FIG. 8 shows gaps or missing image slices for facilitating completion of any image voids.

Referring to FIG. 7, images 62 collected via imaging module 12 (or 52) may be displayed on visualization system 16, and any gaps present in the images may be displayed as shown in FIG. 8. As discussed above, when a user is directed to move imaging module 12 (or 52) to fill any voids, the graphical display of the images and any other indicators, such as arrows etc., would facilitate directing a user to move imaging module 12 (or 52) in a certain direction/manner to efficiently fill the voids. Further, whereas the images of FIGS. 7 and 8 are shown as an orthogonal stack, under typical operation, the images would not be perfectly aligned due to manual operation of imaging module. Thus the images may be displayed in a stack or a fan pattern (with the fan pattern being generated by rotation of an imaging module around an axis orthogonal to a patient's skin, or by tilting of the imaging module along an axis parallel to the patient's skin).

As briefly discussed above, systems such as the EnSite® NavX system (commercially offered by St. Jude Medical, Inc., which is described in detail in commonly owned U.S. Pat. No. 7,263,397 entitled "Method and Apparatus for Catheter Navigation and Location and Mapping in the Heart," issued to Hauck et al., which is hereby incorporated by reference in its entirety) or the Biosense Webster Carto™ System, may be incorporated with imaging systems 10, 50 for providing closed-loop feedback. For example, the volumetric images produced by imaging systems 10, 50 may be utilized in conjunction with the EnSite® NavX visualization, navigation, and mapping system that may be a part of imaging systems 10, 50 or a separate and distinct system that works in conjunction with imaging systems 10, 50. For imaging systems 10, 50, the captured ultrasound data may be used in conjunction with the EnSite® Fusion system (commercially offered by St. Jude Medical, Inc.) if a cardiac geometry model is generated from the ultrasound data. Alternatively, the actual image data may be superimposed on the EnSite® Fusion model as either a 2D cut through plane or as a volume rendered 3D image. If CINE image data is used, the 2D cut through plane and volume rendered 3D image would be 3D and 4D respectively.

Although several embodiments of this invention have been described above with a certain degree of particularity, those skilled in the art could make numerous alterations to the disclosed embodiments without departing from the scope of this invention. All directional references (e.g., upper, lower, upward, downward, left, right, leftward, rightward, top, bottom, above, below, vertical, horizontal, clockwise and counterclockwise) are only used for identification purposes to aid the reader's understanding of the present invention, and do not create limitations, particularly as to the position, orientation, or use of the invention. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not as limiting. Changes in detail or structure may be made without departing from the invention as defined in the appended claims.

What is claimed is:

1. A cardiac imaging system comprising:
    an imaging module including an ultrasound emitter and at least one position marker, the imaging module configured to obtain a plurality of 2D or 3D image slices; and
    a tracking and control system including a position sensing system for sensing a location and orientation of the position marker relative to a predetermined reference wherein the location and orientation of the position marker is indicative of the location and orientation of the imaging module, the tracking and control system operable with the imaging module to produce at least a three dimensional image of a patient's anatomy from the plurality of 2D or 3D image slices and location and orientation of the position marker relative to the predetermined reference; and wherein the tracking and control system is configured to detect omitted areas of the patient's anatomy by determining gaps between corresponding 2D or 3D image slices of the plurality of 2D or 3D image slices, and provide guidance information to position the imaging module to obtain data pertaining to omitted areas of the patient's anatomy, wherein at least a 2D or 3D image slice for the determined gap is obtained by the position of the imaging module obtained from the guidance information to fill the omitted area within a predetermined parameter of accuracy and provide an alert when the omitted area is filled.

2. The cardiac imaging system according to claim 1, wherein the imaging module is a hand-held module disposable against the patient's skin.

3. The cardiac imaging system according to claim 1, wherein the imaging module is operatively connected to a catheter.

4. The cardiac imaging system according to claim 1, wherein the imaging module is a two dimensional imaging module, the third dimension of the three dimensional image produced by the tracking and control system being time.

5. The cardiac imaging system according to claim 1, wherein the imaging module is a three dimensional imaging module, the tracking and control system producing a four dimensional image, with the fourth dimension being time.

6. The cardiac imaging system according to claim 1, wherein the three dimensional image is a CINE image.

7. The cardiac imaging system according to claim 1, wherein the position marker emits an infrared signal sensed by the position sensing system.

8. The cardiac imaging system according to claim 1, wherein the position marker includes at least one optical fiducial marker, and wherein the optical fiducial marker is a spherical marker that reflects infrared light emitted by illuminators on the position sensing system.

9. The cardiac imaging system according to claim 8, further comprising a plurality of the optical fiducial markers disposed in a predetermined arrangement, wherein the predetermined arrangement is one of a generally triangular pyramid-shaped arrangement and a generally symmetrical arrangement.

10. The cardiac imaging system according to claim 8, further comprising at least one further optical fiducial marker disposed against a moving part of the patient's anatomy being imaged, the further optical fiducial marker serving as a moving reference for the position sensing system.

11. The cardiac imaging system according to claim 1, wherein the position marker includes at least one magnetic marker.

12. The cardiac imaging system according to claim 11, further comprising a magnetic emitter operably connected to the position sensing system, the magnetic emitter for emitting a magnetic field for sensing a location and orientation of the magnetic marker.

13. The cardiac imaging system according to claim 1, wherein imaging system is operably connected to a robotic catheter system for automatic cardiac imaging.

14. The cardiac imaging system according to claim 1, wherein the imaging system includes a visualization subsystem for displaying the image of the patient's anatomy.

15. The cardiac imaging system according to claim 1, wherein the tracking and control system automatically aligns a plurality of images obtained by the imaging module relative to the predetermined reference to generate the three dimensional image.

16. The cardiac imaging system according to claim 1, wherein the tracking and control system automatically aligns a plurality of images obtained by the imaging module relative to the predetermined reference to generate a three dimensional time-varying image, the tracking and control system further ascertains gaps in the three dimensional time-varying image, and automatically completes any ascertained gaps.

17. A method of cardiac imaging comprising:
    operatively attaching at least one position marker to an imaging module including an ultrasound emitter configured to obtain a plurality of 2D or 3D image slices;
    sensing a location and orientation of the position marker relative to a predetermined reference wherein the location and orientation of the position marker is indicative of the location and orientation of the imaging module; and
    producing at least a three dimensional image of a patient's anatomy from the plurality of 2D or 3D image slices and location and orientation of the position marker relative to the predetermined reference by evaluating at least one image obtained by the imaging module and aligning the image obtained by the imaging module relative to the location and orientation of the position marker; and wherein a tracking and control system is configured to detect omitted areas of the patient's anatomy by determining gaps between corresponding 2D or 3D image slices of the plurality of 2D or 3D image slices, and provide guidance information to position the imaging module to obtain data pertaining to the omitted areas of the patient's anatomy, wherein at least a 2D or 3D image slice for the determined gap is obtained by the position of the imaging module obtained from the guidance information to fill the omitted area within a predetermined parameter of accuracy and provide an alert when the omitted area is filled.

18. The method according to claim 17, further comprising producing the three dimensional image by processing a plurality of images obtained by the imaging module using automatic segmentation algorithms.

19. The method according to claim 17, further comprising automatically aligning the image obtained by the imaging module relative to the predetermined reference.

20. The cardiac imaging system according to claim 1, wherein the guidance information comprises suggested increased or decreased tilting of the image module.

* * * * *